(12) United States Patent
Schilling et al.

(10) Patent No.: US 8,747,339 B2
(45) Date of Patent: Jun. 10, 2014

(54) CORRECTIVE JOINT

(75) Inventors: Matthias Schilling, Weissenborn-Lüderode (DE); Wissam Jarjour, Lübben (DE)

(73) Assignee: Otto Bock Healthcare GmbH, Duderstadt (DE)

( * ) Notice: Subject to any disclaimer, the term of this patent is extended or adjusted under 35 U.S.C. 154(b) by 318 days.

(21) Appl. No.: 12/746,149

(22) PCT Filed: Dec. 16, 2008

(86) PCT No.: PCT/DE2008/002088
§ 371 (c)(1),
(2), (4) Date: Jun. 3, 2010

(87) PCT Pub. No.: WO2009/079992
PCT Pub. Date: Jul. 2, 2009

(65) Prior Publication Data
US 2010/0262055 A1    Oct. 14, 2010

(30) Foreign Application Priority Data

Dec. 21, 2007  (DE) .......................... 10 2007 062 961

(51) Int. Cl.
*A61F 5/00* (2006.01)
(52) U.S. Cl.
USPC .................................. 602/16; 602/20; 602/23
(58) Field of Classification Search
USPC ................ 602/16, 20–28; 128/878–879, 882; 16/321, 334
See application file for complete search history.

(56) References Cited

U.S. PATENT DOCUMENTS

| 4,433,679 A | 2/1984 | Mauldin et al. |
| 4,697,808 A | 10/1987 | Larson et al. |
| 4,711,242 A | 12/1987 | Petrofsky |

(Continued)

FOREIGN PATENT DOCUMENTS

| DE | 19606092 A1 | 8/1997 |
| DE | 19904554 A1 | 8/2000 |

(Continued)

OTHER PUBLICATIONS

PCT International Search Report for PCT International Application No. PCT/DE2008/002088, dated Aug. 4, 2009.

*Primary Examiner* — Michael A. Brown
(74) *Attorney, Agent, or Firm* — Holland & Hart

(57) ABSTRACT

The invention relates to a joint comprising a first joint arm (1) and a second joint arm (2), which is supported pivotally about a pivot axis (A) on the first joint arm (1) and with the first joint arm (1) encloses a spread angle ($\Phi$), which is between a maximum spread angle ($\Phi_{max}$) and a minimum spread angle ($\Phi_{min}$), which is determined by the design of the joint. According to the invention, a locking device (15), which by moving a bar (8) can selectively be brought into a locking position, in which the first joint arm (1) and the second joint arm (2) are locked relative to each other, a release position, in which the first joint arm (1) and the second joint arm (2) can be pivoted freely relative to each other, and an angle limiting position, in which (i) the first joint arm (1) and the second joint arm (2) can be pivoted relative to each other up to a preset stop spread angle ($\Phi_A$) and (ii) a pivoting motion at larger spread angles ($\Phi$) is blocked.

20 Claims, 7 Drawing Sheets

(56) References Cited

U.S. PATENT DOCUMENTS

| | | |
|---|---|---|
| 5,358,469 A | 10/1994 | Patchel et al. |
| 5,658,241 A | 8/1997 | Deharde et al. |
| 5,749,840 A | 5/1998 | Mitchell et al. |
| 6,993,808 B1 * | 2/2006 | Bennett et al. ............... 16/334 |
| 7,235,059 B2 * | 6/2007 | Mason et al. ................. 602/26 |
| 7,984,531 B2 * | 7/2011 | Moore ........................ 16/326 |

FOREIGN PATENT DOCUMENTS

| | | |
|---|---|---|
| DE | 19933197 B4 | 8/2005 |
| EP | 0302148 A1 | 2/1989 |
| EP | 1579829 A1 | 9/2005 |
| WO | 8300283 A1 | 2/1983 |
| WO | 8700035 A1 | 1/1987 |

* cited by examiner

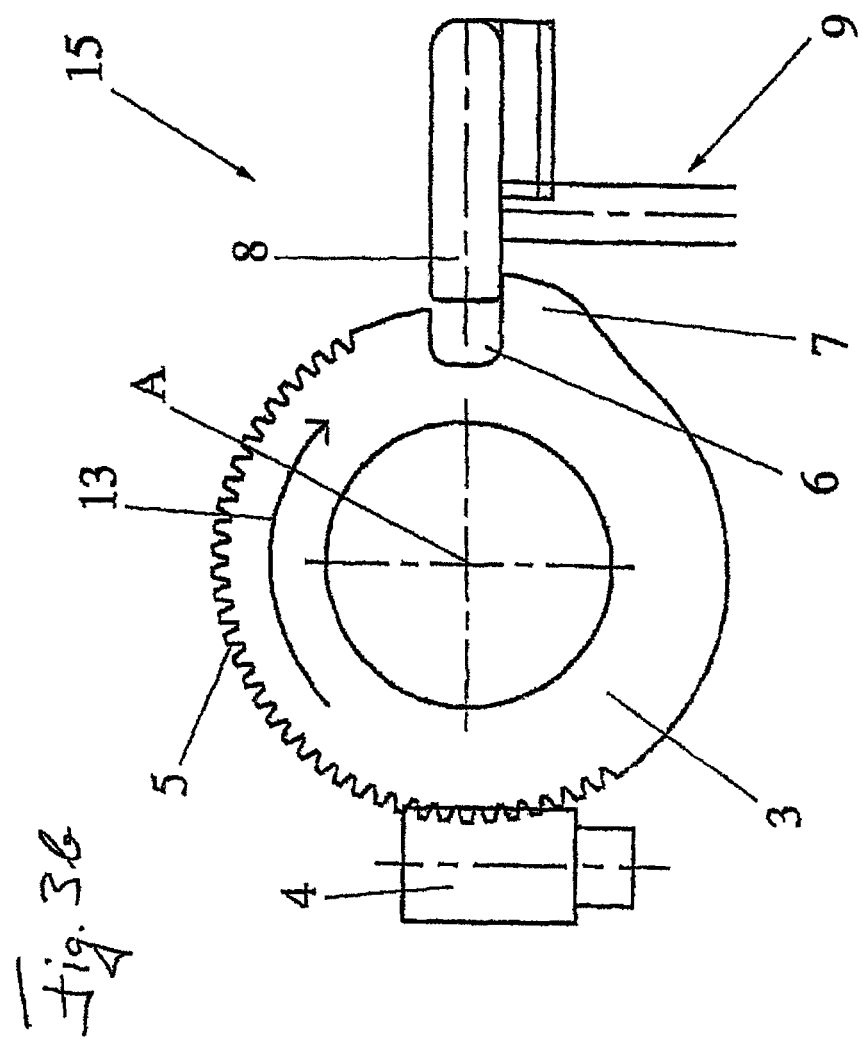

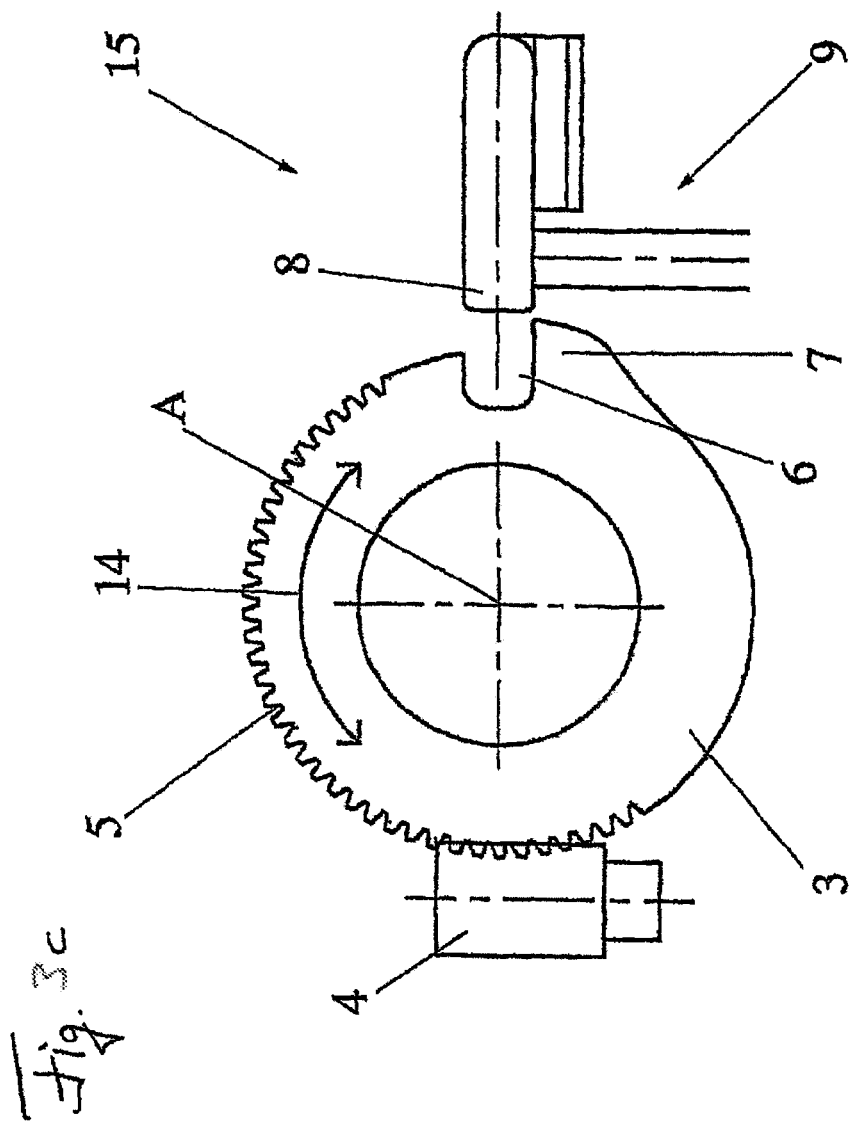

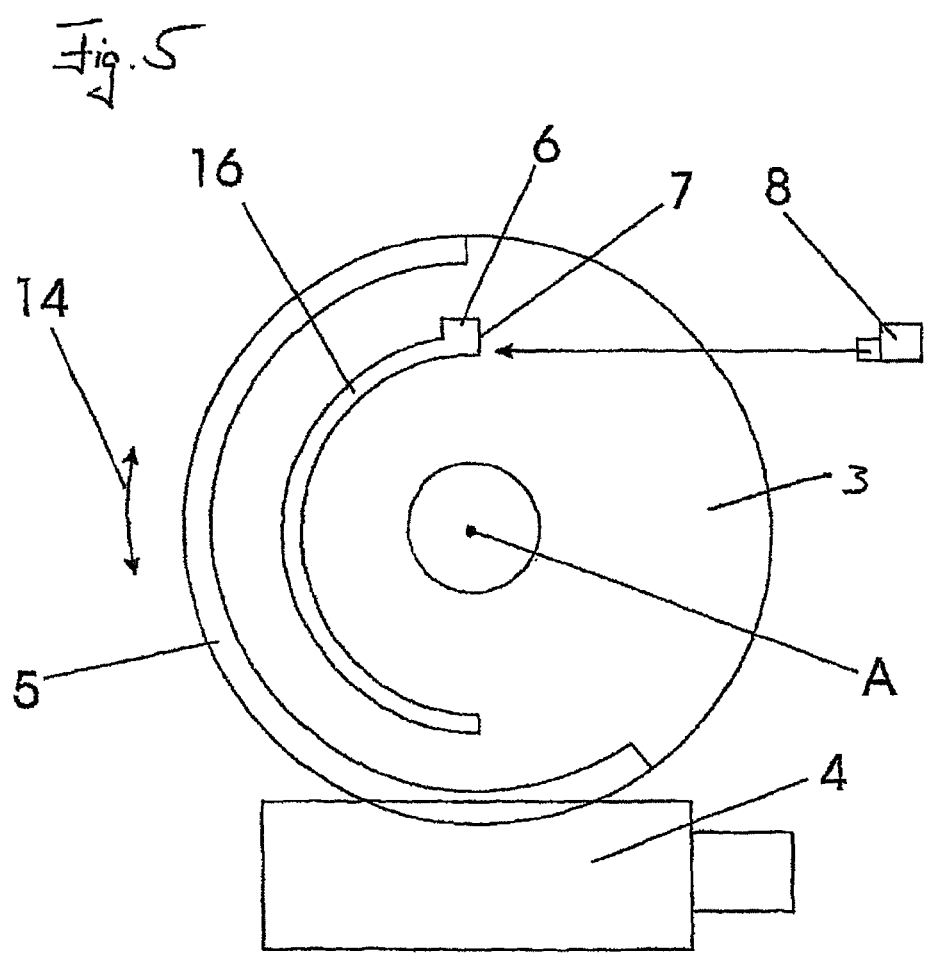

CORRECTIVE JOINT

TECHNICAL FIELD

The invention relates to a joint.

EP 1 579 829 A discloses a joint. The disadvantage of this joint is that it is complicated to attach because the angle has set anew every time it is attached.

BACKGROUND

By way of example, a joint with an adjustable angle is also disclosed in DE 196 06 092 A1 and it is used, for example, in ortheses for different body parts. The two joint arms are provided with holes in the region at which they abut. The holes of the one joint arm and the holes of the second joint arm overlay at certain values of the spread angle included by the two joint arms. In this case, the two pivot arms are interconnected by sticking a pin through the two overlaying holes and the joint is locked. If the pin is removed, the two joint arms can pivot with respect to one another without restrictions.

The pin can also be inserted into holes provided in only one joint arm. In the region of these holes, the other joint arm has a smaller radius from the pivot axis and comprises a stop lug. Said lug butts against the pin at a stop angle determined by the pin. This restricts the possible pivot angle in one direction.

The use of such joints in ortheses for e.g. the knee or elbow allows the corresponding body limbs to be fixed relative to one another in a certain position. The body joint cannot be moved if the orthesis joint is locked. However, the patient finds it practical and more comfortable to be able to pivot the orthesis joint into the desired position for attaching the orthesis.

It is disadvantageous that the locking can only be brought about at certain angular distances and that intermediate settings are not possible. Additionally, the locking procedure itself is also cumbersome and impractical. When the orthesis is applied, the two holes in the joint arms that should be connected by the pin have to be brought into an overlaid position. Additionally, it is difficult to recognize which angle is the correct angle at which the joint should be locked. Therefore, locking can be brought about at the wrong angles.

If the pin is pulled out of the joint in order to reach the release position from the locking position or the angle-limiting position, information relating to the previously set angle is lost. Said angle must, in the case where the joint should again be brought into the locking or angle-limiting position, be set in a cumbersome fashion by inserting the pin into the corresponding hole.

DE 199 04 554 A1 discloses a joint, in which the angular range, through which the first joint arm can be pivoted with respect to the second joint arm, can be set in a step-free fashion. For this, provision is made for two disks, which are connected to a joint arm in a rotationally secure fashion and each have an arc-shaped slot. A transverse pin that engages into the two slots is attached to the other joint arm. The two disks can be displaced with respect to one another by rotation about the pivot axis of the joint. This changes the region in which both slits are overlaid and in which the transverse pin, and hence the other joint arm, moves.

It is disadvantageous that the joint described in said document cannot simply be brought into a locking position or a release position. For this, the disks have to be displaced against one another in such a way that the region of overlay of the two slots is minimal or maximal. Since the disks are displaced by rotating a worm engaging in teeth provided on the disk, this change is cumbersome and long-winded. Moreover, information relating to the previously set angular range is also lost in this case.

DE 199 33 197 discloses a joint in which the two joint arms can be pivoted against one another over an adjustable angular region. For this, holes are provided in plates at intervals of in each case 15°, and stop elements can be inserted into said holes. This can be brought about in both pivot directions, and so the possible pivot region is restricted in both directions by the stop elements. The angle between the two stop surfaces, which butt against the respective stop elements, can only be adjusted in a step-free fashion over a region of 15°. This affords the possibility of adjusting, in a step-free fashion, the pivot region in which the two joint arms can be pivoted relative to one another.

The two joint arms can only be locked by selecting the pivot region such that the stop surfaces butt against the respective stop elements on both sides. It follows that the two joint arms can only be locked relative to one another at intervals of in each case 15°.

SUMMARY

Thus, the object of the invention is to provide a joint, whose locking position can be set in a simple reproducible manner, and which has an adjustment option in which the movement is made possible up to a certain stop angle.

The invention solves the problem by means of a generic joint comprising a locking device which, by movement of a bar, can be brought into a locking position, in which the first joint arm and the second joint arm are locked relative to one another, a release position, in which the first joint arm and the second joint arm can be pivoted relative to one another without restrictions, and an angle-limiting position, in which the first joint arm and the second joint arm can be pivoted with respect to one another up to a predetermined stop spread angle and pivoting to larger angles of spread is blocked.

It is advantageous that the stop spread angle has to be set once to the desired value and thereafter it is only the position of the locking device that has to be changed in order to switch between locking position, release position and angle-limiting position. The predetermined stop spread angle remains set in the process, and so it is even possible to switch from the release position to the angle-limiting position or locking position of the locking device in a simple, quick and reproducible fashion.

The locking apparatus preferably comprises a stop spread angle adjustment device, which is arranged on the first joint arm in a definably rotationally secured fashion and has a stop, for example in the form of a stop lug, and a recess, and comprises a bar arranged on the second joint arm and can be brought into the locking position by inserting the bar into the recess, can be brought into the angle-limiting position by spacing the bar from the recess, and can be brought into the release position by spacing the bar further from the recess.

In particular, a definably rotationally secured fashion means that the stop spread angle adjustment device is arranged on the first joint arm in a rotationally secured fashion, but its position relative to the first joint arm can be adjusted.

Here, the recess in the stop spread angle adjustment device can be designed as e.g. a groove or a bore. The designation "bar" in this case does not mean a particular geometric shape or a certain movement direction in which the bar is moved away from the recess. The designation "bar" merely names the functional principle of the component. The bar can move away from the recess in a radial or axial direction with respect to the pivot axis (A). In order to change the position of the bar, an adjustment element is provided on the second joint arm, which element is, for example, a sliding controller by means of which the bar can be brought into the various positions.

In another embodiment, the locking device comprises a stop spread angle adjustment device, wherein a bar is arranged on the first joint arm in a definably rotationally secured fashion, and has, arranged on the second joint arm, a stop and a recess. The stop spread angle adjustment device can be brought into the locking position by restricting the bar by the recess or by making the bar and the recess engage, can be brought into the angle-limiting position by spacing the recess from the bar, and can be brought into the release position by spacing the recess further from the bar.

In other words, in this variant the bar is arranged on the spread angle adjustment device in a rotationally secured fashion. For adjustment purposes, the stop and/or the recess is displaced relative to the bar.

Advantageously, the stop spread angle adjustment device is designed as an intermediate disk with a substantially circular upper side, a substantially circular lower side substantially parallel to the upper side, and a circumferential surface on which the stop and the recess is arranged.

Advantageously, if the locking device is in the angle-limiting position and the first joint arm and the second joint arm include the stop spread angle, the bar butts against the stop and so pivoting of the first joint arm relative to the second joint arm is blocked beyond the stop spread angle. Pivoting to smaller angles is possible and not influenced by the position of the bar relative to the stop. This means that the locking device is in the angle-limiting position if, whilst pivoting the first joint arm relative to the second arm joint, the bar butts against the stop when the spread angle is intended to be increased beyond the stop spread angle.

The bar advantageously engages into the recess substantially without play if the locking apparatus is in the locking position. Substantially without play means that it is not necessary for the bar to be without play in the mathematical sense. For example, it suffices for the possible pivot angle of the first joint arm for example to be less than 1° relative to the second joint arm when the locking device is in the locking position.

In a preferred embodiment, the intermediate disk has teeth over at least a part of its circumference and the locking apparatus comprises a worm, which is arranged on the first joint arm and meshes with the teeth of the intermediate disk. It is particularly advantageous for the worm to mesh with the teeth of the intermediate disk in a self-locking fashion. This ensures that the intermediate disk is mounted on the first joint arm in a rotationally secured fashion that can be adjusted. A rotation of the worm changes, in a step-free fashion, the position of the intermediate disk relative to the first joint arm, and thus the position of the stop and the recess of the intermediate disk as well, and therefore the stop spread angle. The rotationally secured mounting of the intermediate disk on the first joint arm ensures that the stop spread angle thus set remains unchanged as long as there is no actuation of the worm. In order to prevent inadvertent rotation of the worm, it is advantageously necessary to use a tool, e.g. an Allen key, to rotate the worm. For this, one end of a shaft on which the worm is mounted in a rotationally secured fashion is equipped with an interlocking element, for example a hexagon socket.

The stop is advantageously formed by a region of the intermediate disk protruding radially from the pivot axis (A). Here, the side of the stop provided for the abutment of the bar preferably has a straight design. As a result of this, no radial forces are generated when the bar butts against the stop.

The opposite side of the stop in terms of the circumferential direction has a ramp-shaped design. This means that the radial extent of the intermediate disk continuously increases in this region. This ensures that, in the case where the locking device is brought into the angle-limiting position from the release position while the spread angle between the first joint arm and the second joint arm is greater than the set stop spread angle, pivoting of the first joint arm relative to the second joint arm is possible over the region of the predetermined stop spread angle, and the bar is slightly pushed out of the angle-limiting position in the process.

The bar is preferably equipped with a spring structure such that in this case it snaps back into the angle-limiting position after the stop spread angle has been passed.

Advantageously, the recess and the stop directly adjoin one another along the circumference of the intermediate disk. This ensures in a particularly simple fashion that the stop spread angle is also that spread angle at which the joint can be locked.

In a preferred refinement, the joint comprises a second locking device, which can be brought into an angle-limiting position, in which the first joint arm and the second joint arm can be pivoted with respect to one another up to a predetermined second stop spread angle and pivoting to smaller angles of spread is blocked. Here, provision is preferably made for the second locking device also to have an intermediate disk, which can be brought into an angle-limiting position by means of a second bar provided for this. This second bar is preferably provided on the second joint arm like the first bar. The second intermediate disk can also be adjusted in a step-free fashion relative to the first joint arm by means of a second worm provided for this. Since the second locking device in the angle-limiting position prevents the pivoting of the first joint arm relative to the second joint arm toward smaller angles than the predetermined second stop spread angle, the region in which the first joint arm can be pivoted relative to the second joint arm can thus be restricted in a step-free fashion on both sides. Of course, the two bars and the two worms can also be provided on respectively different joint arms as long as the bar and worm belonging to one locking device are arranged on different joint arms.

Advantageously, an orthesis has a first receptacle device for a first body limb and a second receptacle device for a second body limb, which are connected to one another such that they can pivot by means of at least one joint described above, and include an orthesis angle. The advantage of such an orthesis is that the joint can be brought into the release position for attaching the orthesis, and so the orthesis can be attached in a comfortable and simple fashion and the orthesis can then either be locked at a certain orthesis angle or permit pivoting of the first receptacle device relative to the second receptacle device up to the predetermined stop spread angle in a quick, easy and reproducible fashion. Here, the switch-over is brought about by simply bringing the bar of the locking device into the respectively desired position. In the process, the stop spread angle can be predetermined before the orthesis is applied.

The first receptacle device and the second receptacle device are preferably connected by at least one second joint described above and the first joint limits the pivoting of the first receptacle device relative to the second receptacle device in one direction in the angle-limiting position, and the second joint limits the pivoting of the first receptacle device relative to the second receptacle device in another direction in the angle-limiting position. If both joints are in the respective angle-limiting positions, pivoting of the first receptacle device relative to the second receptacle device is therefore only possible between the two predetermined angles-of-spread of the stops of the two joints.

The orthesis is particularly advantageously a knee or elbow orthesis.

BRIEF DESCRIPTION OF THE DRAWINGS

A preferred exemplary embodiment of the invention will now be described with the aid of the drawing, in which:

FIG. 3b shows a plan view of the locking device according to FIG. 3a in the angle-limiting position, FIG. 3c shows a plan view of the locking device according to FIGS. 3a and 3b in the release position.

FIG. 5 shows a schematic plan view of a locking device according to another embodiment of the invention.

DETAILED DESCRIPTION

Figure 1:
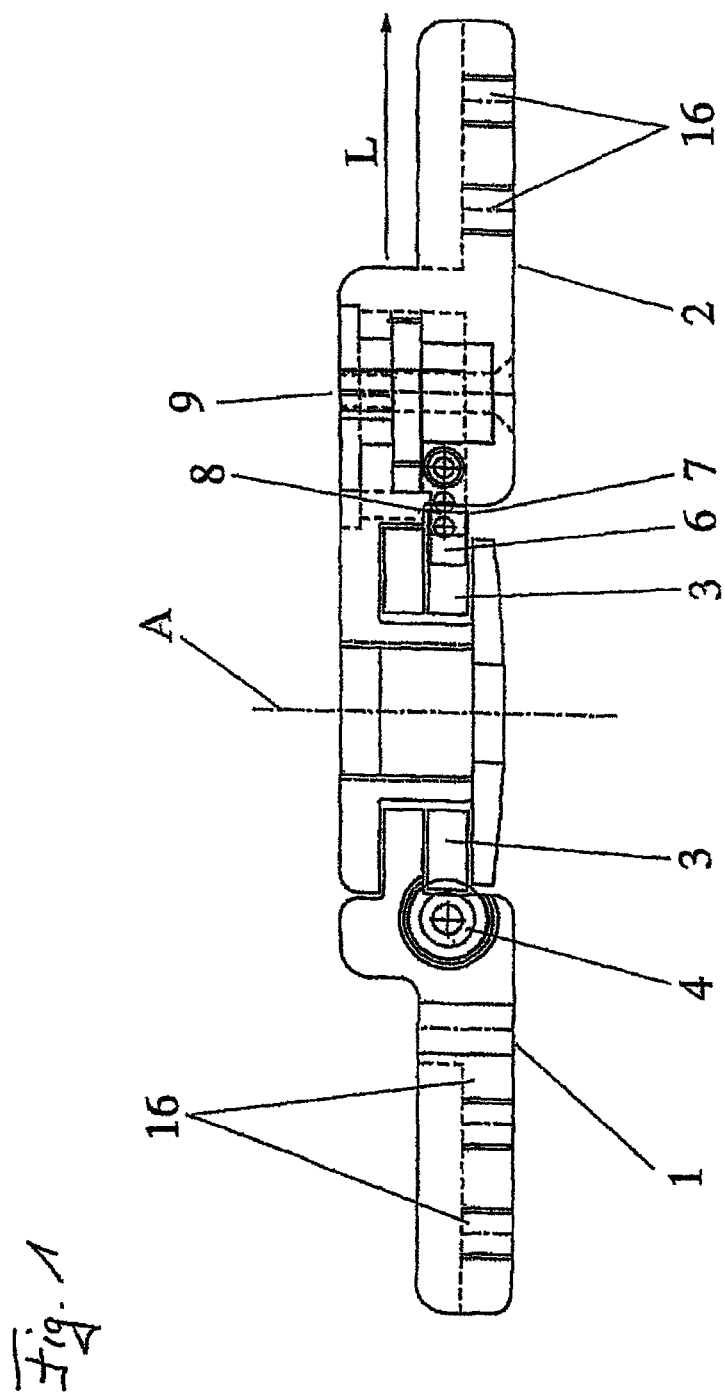
FIG. 1 shows the side view of a joint according to the invention.

FIG. 1 shows a side view of a joint of a preferred embodiment of the invention. A first joint arm 1 and a second joint arm 2 are mounted on one another such that they can pivot about a pivot axis A. The two joint arms have connection apparatuses 16. Moreover, they can for example be connected with cuffs, which can be attached to various body parts. Here, it is possible for the cuffs to be able to be attached to the respective body part using for example hook-and-loop fasteners or other reversibly closable attachment means. By way of example, this is an upper arm or forearm. The cuffs have connection means, which make them connectable to the connection means 16 on the joint arms 1, 2.

An intermediate disk 3 is mounted on the first joint arm 1 in a rotationally secured fashion such that it can be adjusted. The intermediate disk 3 has a substantially disk-shaped base body with an upper side, a lower side substantially parallel to the upper side, and a circumferential surface arranged between the upper side and the lower side. The upper side and the lower side of the intermediate disk 3 have a substantially circular design. The intermediate disk 3 has a central bore, with the pivot axis A running through the center thereof when the intermediate disk is connected to the first joint arm. The intermediate disk can be pivoted with the first joint arm about the pivot axis A.

The intermediate disk 3 has, over at least part of its circumference, teeth 5 arranged radially outwardly, a stop 7 in the form of a stop lug and a recess 6.

A worm 4 is arranged in the first joint arm 1. This worm is mounted in a rotationally secure fashion on a shaft 11, the one end of which is for example provided with an interlocking element such as a hexagon socket. The worm 4 meshes with the teeth 5 of the intermediate disk 3. Rotation of the shaft 11, and thus of the worm 4, changes the position of the intermediate disk 3 relative to the worm 4. As a result, the intermediate disk 3 is rotated about the pivot axis A. This also changes the position of the recess 6 and the stop lug 7 relative to the first joint arm 1. This change is brought about in a step-free fashion because the worm 4 can also be rotated in a step-free fashion.

A bar 8 is arranged in the second joint arm 2 in a displaceable fashion. This bar can be displaced by means of an adjustment device 9, which is likewise arranged on the second joint arm 2. Here, the displacement is brought about in a parallel fashion with respect to the longitudinal direction L of the second joint arm 2.

Figure 2:
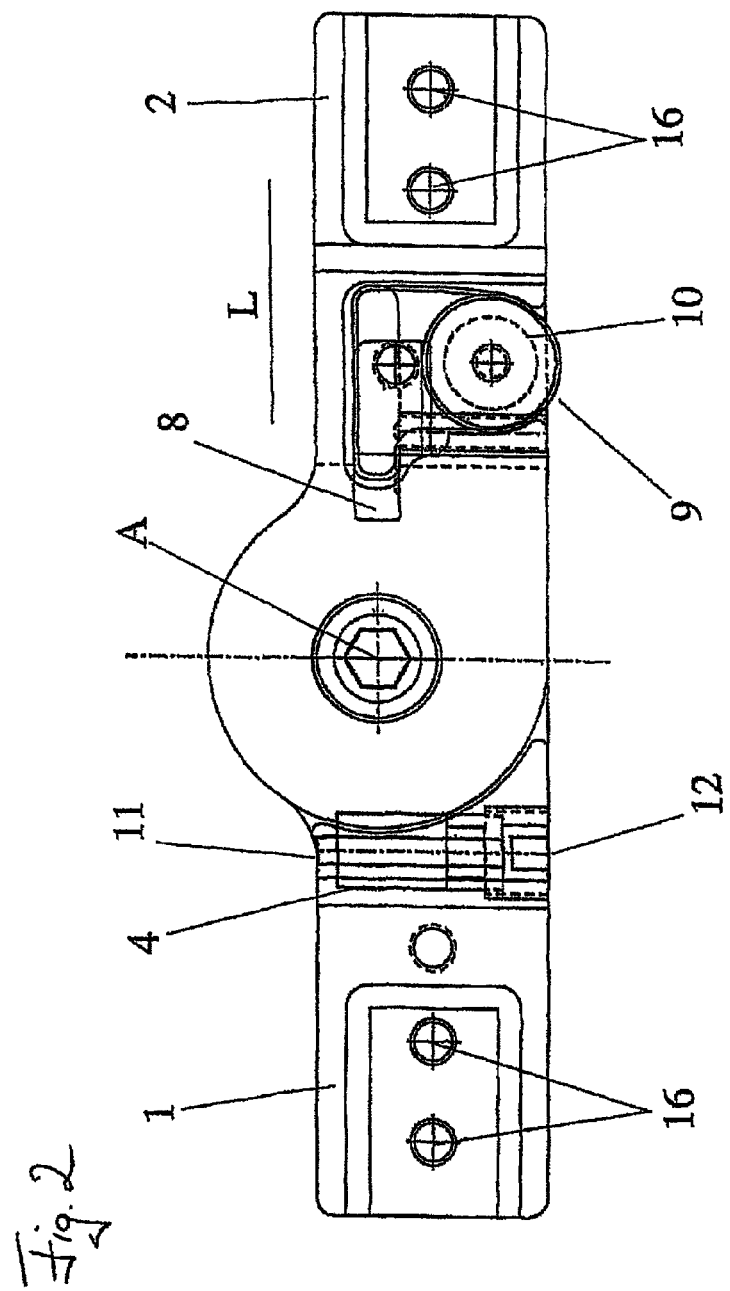
FIG. 2 shows a plan view of the joint according to FIG. 1.

FIG. 2 shows a plan view of the joint shown in a side view in FIG. 1. The first joint arm 1 and the second joint arm 2 are mounted such that they can pivot about the pivot axis A, which projects out of the plane of the image in FIG. 2. The bar 8 can be brought into various positions in the second joint arm 2 by means of the adjustment device 9. The adjustment device 9 comprises an adjustment wheel 10, the rotational movement of which is converted into a movement of the bar 8 in a radial direction with respect to the pivot axis A.

Figure 3A:
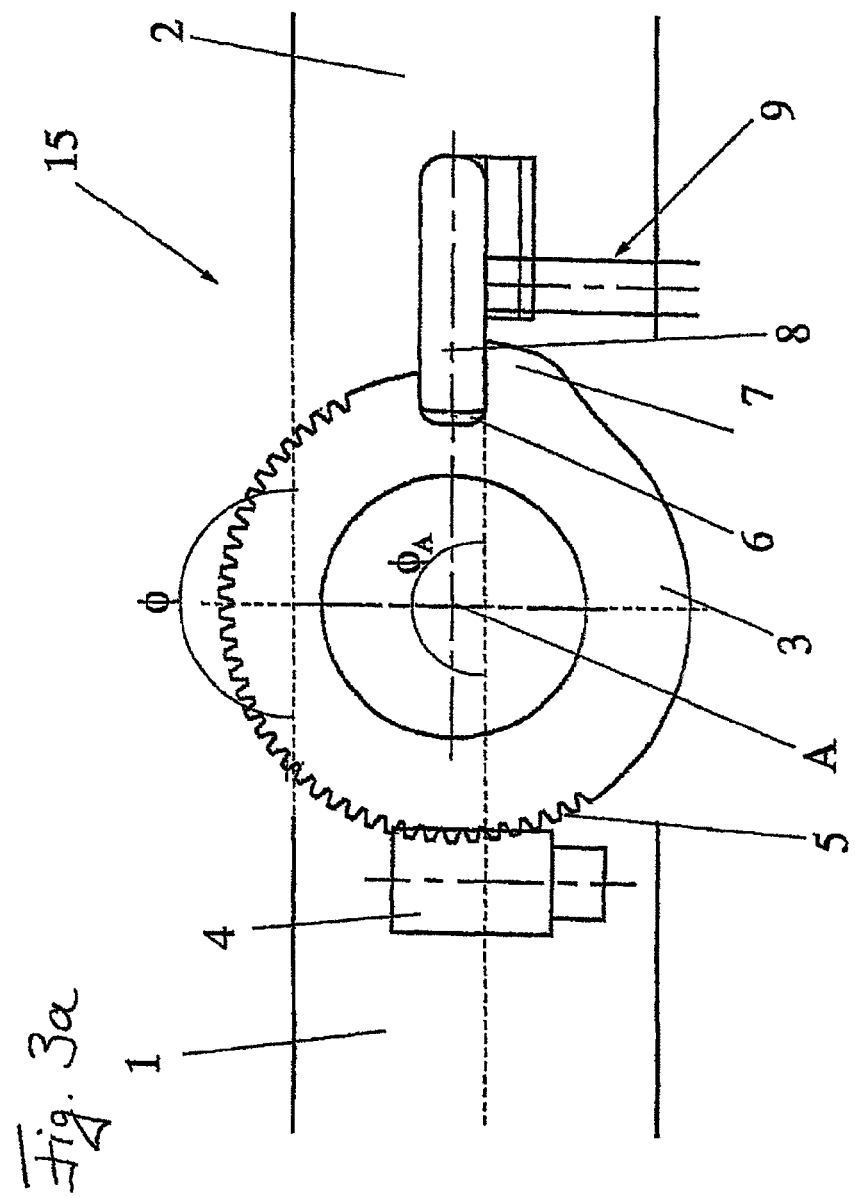
FIG. 3a shows a plan view of the locking device of the joint according to FIGS. 1 and 2 in the locking position.

FIGS. 3a to 3c each show a locking device 15 in the various positions. The intermediate disk 3 is shown in each case, and it has teeth 5 along at least a part of its circumference into which the worm 4 engages.

In FIG. 3a, the first and the second joint arm 1, 2 are indicated by thick full lines. The spread angle ϕ is included between the two joint arms 1, 2. The stop spread angle $\Phi_A$ is included between the stop lug 7 and the first joint arm 1. In FIG. 3a, both the two joint arms 1, 2 and the edge of the stop lug 7, against which the bar 8 butts, are parallel. Therefore, the angles $\Phi$, $\Phi_A$ are drawn together for better clarity. In the illustrated example, both angles are 180°.

In FIG. 3a, the locking device is in the locking position. The bar 8 engages into the recess 6 of the intermediate disk 3. Pivoting of the intermediate disk 3 relative to the bar 8 is not possible. Since the intermediate disk is arranged in a rotationally secure fashion on the first joint arm 1 and the bar 8 is arranged in a rotationally secure fashion on the second joint arm 2, pivoting of the two joint arms 1, 2 relative to one another is not possible either.

Rotating the shaft 11 on which the worm 4 is mounted in a rotationally secured fashion leads to rotation of the intermediate disk 3 relative to the worm 4. Thus, this also changes the position of the recess 6 and the stop lug 7 relative to the worm, and hence to the first joint arm 1 on which the worm 4 is attached. In the locking position of the locking device 15, the bar 8 engages into the recess 6. Therefore, the position of the second joint arm 2 relative to the first joint arm 1 also changes when the worm is rotated. This changes the angle by locking the joint.

In FIG. 3b, the locking device 15 is in the angle-limiting position. The stop spread angle $\Phi_A$ is included between the first joint arm 1 and the second joint arm 2 (neither of which is illustrated). Therefore, the bar 8 butts against the stop lug 7. Pivoting of the intermediate disk relative to the bar 8 is only possible in one direction in FIG. 3b, namely toward smaller angles of spread $\Phi$. This is indicated in FIG. 3b by the arrow 13. Pivoting is prevented in the opposite direction by the bar 8 butting against the stop lug 7. In the position shown, both the spread angle $\Phi$ and the stop spread angle $\Phi_A$ are 180°. Neither is illustrated for reasons of clarity.

The position of the intermediate disk 3 relative to the first joint arm 1 is changed by rotating the worm 4, as in the locking position shown in FIG. 3a. The rotation of the intermediate disk 3 about the pivot axis A associated with this also changes the stop spread angle $\Phi_A$ included between the stop lug 7 and the first joint arm.

FIG. 3c shows a locking device 15 in the release position. Pivoting of the first joint arm 1 relative to the second joint arm 2 is possible in both directions without restrictions. This is indicated in FIG. 3c by the double-headed arrow 14. Although rotation of the worm 4 changes the position of the stop lug 7 relative to the first joint arm 1, this has no influence on the ability of the first joint arm 1 to pivot relative to the second joint arm 2. Possible angles of spread $\Phi$ are angles that are both greater and less than the predetermined stop spread angle $\Phi_A$. However, if the locking device 15 is again brought from the release position into the angle-limiting position or the locking position, the limiting of the possible pivot movements is again given by the stop lug 7 and the recess 6, without the stop spread angle $\Phi_A$ having to be set anew.

Figure 4:
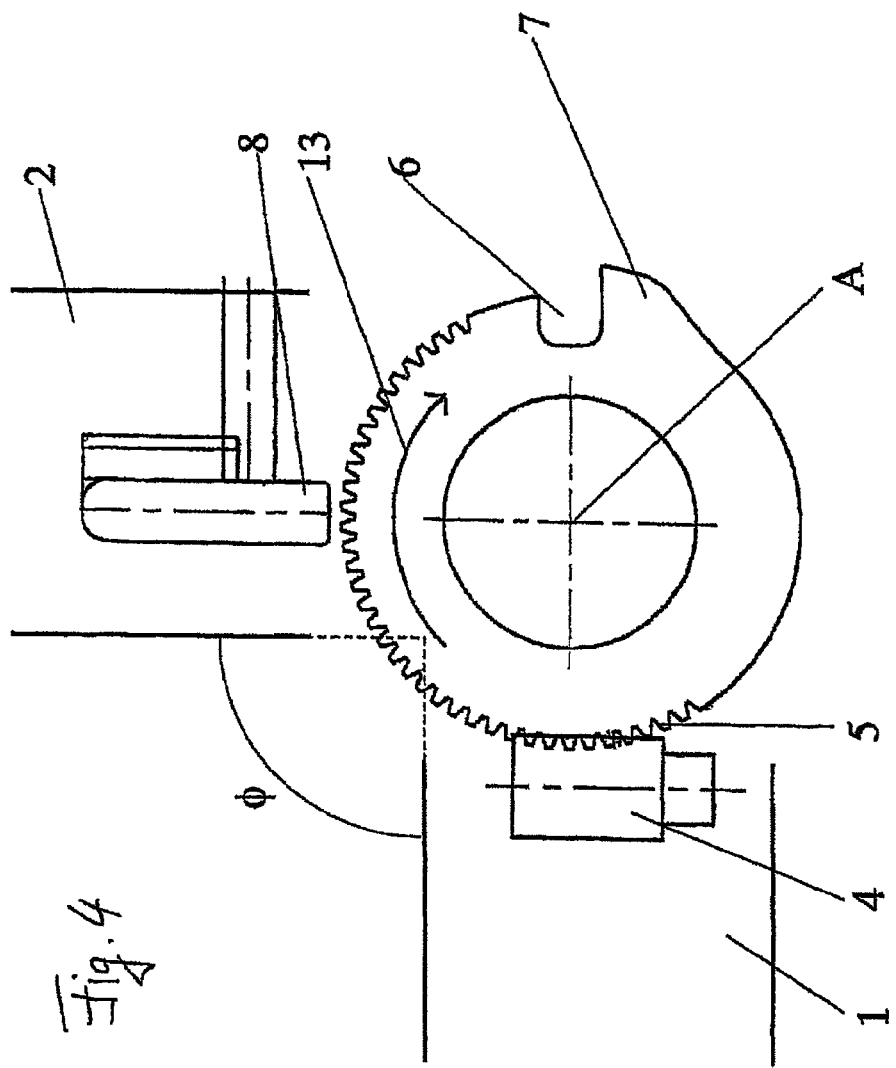
FIG. 4 shows a plan view of a locking device according to FIG. 3b, in which the spread angle is not the stop spread angle.

FIG. 4 shows a locking device 15 in the angle-limiting position. Like in FIG. 3*b*, the stop spread angle $\Phi_A$ is 180°, since the position of the intermediate disk 3 relative to the worm 4 and hence to the first joint arm 1 is unchanged. The first joint arm 1 and the second joint arm 2 are indicated in FIG. 4 by thick solid lines. In FIG. 4, the second joint arm 2 is pivoted with respect to the first joint arm 1. This is only possible at angles of spread $\Phi$ that are smaller than the predetermined stop spread angle $\Phi_A$. The spread angle $\Phi$ included between the first joint arm 1 and the second joint arm 2 is 90° in FIG. 4.

FIG. 5 shows a plan view of a locking device 15. An intermediate disk 3 is shown, on the edge of which the teeth 5 are located, which are indicated by a stripe in FIG. 5. The teeth 5 engage into a worm 4 and so the position of the intermediate disk 3 can be adjusted relative to the joint arm on which it is arranged. The joint arm is not shown in FIG. 5.

In the embodiment shown in FIG. 5, the intermediate disk 3 has a slit 16 running concentrically to the pivot axis. The slit 16 has the recess 6 at its one end. The stop 7 is formed by a marginal limiting of slit 16 in the rotational direction. The bar 8 is mounted such that it can move in a direction parallel to the pivot axis A. In FIG. 5, the bar 8 is thus moved out of the plane of the drawing, or into it.

If the bar 8 is in its lowered position, it engages into the recess 6 with the right-hand component in FIG. 5. This component of the bar 8 is designed such that it is too large to engage into the slit 16 beyond the recess 6. Moving the intermediate disk 3 relative to the bar 8 is not possible in this position of the bar 8. Therefore, the locking device 15 is in the locking position.

By spacing the bar 8 from the recess 6, that is to say by moving the bar 8 upward in the illustrated example, the bar 8 only engages into the slit 16 with its left-hand component in FIG. 5. The intermediate disk 3 can only be pivoted relative to the bar 8. Only when the previously set stop spread angle (not illustrated) is reached does the bar 8 butt against the stop 7 and movement beyond this spread angle is not possible. The locking device 15 is in the angle-limiting position.

Further spacing of the bar 8 from the recess 6, that is to say further upward movement of the bar 8 in FIG. 5, results in bar 8 and intermediate disk 3 no longer being operatively connected. Pivoting of the intermediate disk 3 relative to the bar 8 and thus of the two joint arms connected to these parts in a rotationally secured fashion is possible without restrictions. The locking device 15 is in the release position.

LIST OF REFERENCE SIGNS

A Pivot axis
$\Phi$ Spread angle
$\Phi_A$ Stop spread angle
1 First joint arm
2 Second joint arm
3 Intermediate disk
4 Worm
5 Teeth
6 Recess
7 Stop
8 Bar
9 Adjustment device
10 Adjustment wheel
11 Shaft
12 Interlocking element
13 Arrow
14 Double-headed arrow
15 Locking device
16 Slit

The invention claimed is:

1. A joint, comprising:
   (a) a first joint arm,
   (b) a second joint arm,
      which is mounted on the first joint arm such that it can pivot about a pivot axis and
      which includes a spread angle with the first joint arm, which angle lies between a maximum spread angle and a minimum spread angle, determined by the design of the joint,
   (c) a locking device, which, by movement of a single bar, can selectively be brought into
      a locking position, in which the first joint arm and the second joint arm are locked relative to one another,
      a release position, in which the first joint arm and the second joint arm can be pivoted relative to one another without restrictions between the minimum spread angle and said maximum spread angle, and
      an angle-limiting position, in which
         (i) the first joint arm and the second joint arm can be pivoted with respect to one another up to a predetermined stop spread angle, which is smaller than the maximum spread angle, and
         (ii) pivoting to spread angles larger than the stop spread angle is blocked;
      wherein the locking device comprises
         (i) a stop spread angle adjustment device,
         (i) the bar is arranged on the first joint arm in a definably rotationally secured fashion,
         (ii) a stop and a recess are arranged on the second joint arm, and
         (iii) the locking device can be brought into the locking position by engaging the bar in the recess, can be brought into the angle-limiting position by spacing the bar from the recess, and can be brought into the release position by spacing the bar further from the recess.

2. The joint as claimed in claim 1, wherein the stop spread angle adjustment device is arranged on the second joint arm in a definably rotationally secured fashion and includes the stop and the recess.

3. The joint as claimed in claim 2, wherein the stop spread angle adjustment device is designed as an intermediate disk with
   a substantially circular upper side,
   a substantially circular lower side substantially parallel to the upper side, and
   a circumferential surface on which the stop and the recess or the bar is arranged.

4. The joint as claimed in claim 2, wherein, if
   the locking device is in the angle-limiting position and
   the first joint arm and the second joint arm include the stop spread angle,
   the bar butts against the stop and so pivoting of the first joint arm relative to the second joint arm is blocked beyond the stop spread angle.

5. The joint as claimed in claim 2, wherein the bar engages into the recess substantially without play if the locking apparatus is in the locking position.

6. The joint as claimed in claim 2, wherein the stop spread angle adjustment device is designed as an intermediate disk, and
- the intermediate disk has teeth over at least a part of its circumference and
- the locking apparatus comprises a worm, which is arranged on the first joint arm and meshes with the teeth of the intermediate disk.

7. The joint as claimed in claim 6, wherein
- the intermediate disk has teeth over at least a part of its circumference and
- the locking apparatus comprises a worm, which is arranged on the first joint arm and meshes with the teeth of the intermediate disk, wherein the worm meshes with the teeth of the intermediate disk in a self-locking fashion.

8. The joint as claimed in claim 2, wherein the stop spread angle adjustment device is designed as an intermediate disk, and the stop is formed by a region of the intermediate disk protruding radially from the pivot axis.

9. The joint as claimed in claim 2, wherein the stop spread angle adjustment device is designed as an intermediate disk, and along the circumference of the intermediate disk,
- the recess and
- the stop directly adjoin one another.

10. The joint as claimed in claim 1, wherein the joint comprises a second locking device, which can be brought into an angle-limiting position, in which
- the first joint arm and the second joint arm can be pivoted with respect to one another up to a predetermined second stop spread angle and
- pivoting to smaller spread angles is blocked.

11. An orthesis with
- (a) a first receptacle device for a first body limb and
- (b) a second receptacle device for a second body limb, which
  - are connected to one another such that they can pivot by means of at least one joint as claimed in claim 1, and include an orthesis angle.

12. The joint as claimed in claim 1, wherein the stop spread angle adjustment device is designed as an intermediate disk, and
- the intermediate disk has teeth over at least a part of its circumference and
- the locking apparatus comprises a worm, which is arranged on the first joint arm and meshes with the teeth of the intermediate disk.

13. The orthesis as claimed in claim 12, wherein the first receptacle device and the second receptacle device are connected by at least one second joint as claimed in claim 1 and in that
- the first joint limits the pivoting of the first receptacle device relative to the second receptacle device in one direction in the angle-limiting position, and
- the second joint limits the pivoting of the first receptacle device relative to the second receptacle device in another direction in the angle-limiting position.

14. The orthesis as claimed in claim 12, wherein it is a knee or elbow orthesis.

15. The joint as claimed in claim 12, wherein the worm meshes with the teeth of the intermediate disk in a self-locking fashion.

16. The joint as claimed in claim 1, wherein the stop spread angle adjustment device is designed as an intermediate disk with
- a substantially circular upper side,
- a substantially circular lower side substantially parallel to the upper side, and
- a circumferential surface on which the stop and the recess or the bar is arranged.

17. The joint as claimed in claim 1, wherein, if
- the locking device is in the angle-limiting position and
- the first joint arm and the second joint arm include the stop spread angle,
- the bar butts against the stop such that pivoting of the first joint arm relative to the second joint arm is blocked beyond the stop spread angle.

18. The joint as claimed in claim 1, wherein the bar engages into the recess substantially without play if the locking apparatus is in the locking position.

19. The joint as claimed in claim 1, wherein the stop is formed by a region of the intermediate disk protruding radially from the pivot axis.

20. The joint as claimed in claim 1, wherein the stop spread angle adjustment device is designed as an intermediate disk, and along the circumference of the intermediate disk,
- the recess and
- the stop directly adjoin one another.

* * * * *